(12) United States Patent
Markesbery et al.

(10) Patent No.: US 9,861,102 B2
(45) Date of Patent: Jan. 9, 2018

(54) METHODS FOR DISINFECTION (71) Applicants: W. Russell Markesbery, Hebron, KY (US); Eugene J. Pancheri, Cincinnati, OH (US)

(72) Inventors: W. Russell Markesbery, Hebron, KY (US); Eugene J. Pancheri, Cincinnati, OH (US)

(73) Assignee: Markesbery Blue Pearl LLC, Cincinnati, OH (US)

( * ) Notice: Subject to any disclaimer, the term of this patent is extended or adjusted under 35 U.S.C. 154(b) by 0 days.

(21) Appl. No.: 15/400,371

(22) Filed: Jan. 6, 2017

(65) Prior Publication Data

US 2017/0354144 A1 Dec. 14, 2017

Related U.S. Application Data

(60) Provisional application No. 62/341,799, filed on May 26, 2016.

(51) Int. Cl.
*A61L 2/00* (2006.01)
*B08B 3/00* (2006.01)
(Continued)

(52) U.S. Cl.
CPC .............. *A01N 37/16* (2013.01); *A01N 59/00* (2013.01); *A61L 2/186* (2013.01)

(58) Field of Classification Search
CPC .............. A61L 2/00; A61L 2/0088; A61L 2/16
(Continued)

(56) References Cited

U.S. PATENT DOCUMENTS 5,743,251 A 4/1998 Howell et al.
6,234,167 B1 5/2001 Cox et al.
(Continued)

FOREIGN PATENT DOCUMENTS

GB 2469018 A 10/2010
WO 97/46626 A1 12/1997
(Continued)

OTHER PUBLICATIONS

Zhao, Xuebing, et al., "Preparation of Peracetic Acid from Hydrogen Peroxide Part I : Kinetics for Peracetic Acid Synthesis and Hydrolysis", Journal of Molecular Catalysis A : Chemical, vol. 271, Mar. 12, 2007, (7 pages).
(Continued)

*Primary Examiner* — Monzer R Chorbaji
(74) *Attorney, Agent, or Firm* — Hasse & Nesbitt LLC; Daniel F. Nesbitt (57) ABSTRACT

The present disclosure relates to methods and system for disinfecting surfaces within an area by forming peracids in a reaction layer in situ on the surfaces to be disinfected. Aqueous compositions comprising peracid reactant compounds, particularly hydrogen peroxide and acetic acid, are sequentially dispersed into the area, preventing peracids from being formed until the two peracid reactant compounds contact each other on the surface to be disinfected. Additionally, aqueous compositions containing peracid reactant compounds can further comprise ethanol to both decrease the surface tension of the droplets and enhance the reactants' biocidal activity. Peracid reactant compounds can be sequentially dispersed as electrostatically-charged droplets, so that droplets of a first aqueous composition containing at least one peracid reactant compound are dispersed with a polarity opposite that of a subsequently-applied second aqueous composition compound, driving formation of a peracid on the surface in situ.

30 Claims, 4 Drawing Sheets

(51) Int. Cl.
 *A01N 37/16* (2006.01)
 *A61L 2/18* (2006.01)
 *A01N 59/00* (2006.01)
(58) Field of Classification Search
 USPC .................................. 422/28; 134/26, 28
 See application file for complete search history.

(56) References Cited

U.S. PATENT DOCUMENTS

| | | | |
|---|---|---|---|
| 6,491,233 | B2 | 12/2002 | Nichols |
| 6,501,052 | B2 | 12/2002 | Cox et al. |
| 6,516,796 | B1 | 2/2003 | Cox et al. |
| 6,557,552 | B1 | 5/2003 | Cox et al. |
| 6,568,390 | B2 | 5/2003 | Nichols et al. |
| 6,640,050 | B2 | 10/2003 | Nichols et al. |
| 6,681,769 | B2 | 1/2004 | Sprinkel, Jr. et al. |
| 6,681,998 | B2 | 1/2004 | Sharpe et al. |
| 6,692,694 | B1 | 2/2004 | Curry et al. |
| 6,701,921 | B2 | 3/2004 | Sprinkel, Jr. et al. |
| 6,715,487 | B2 | 4/2004 | Nichols et al. |
| 6,766,220 | B2 | 7/2004 | McRae et al. |
| 6,772,757 | B2 | 8/2004 | Sprinkel, Jr. |
| 6,799,572 | B2 | 10/2004 | Nichols et al. |
| 6,804,458 | B2 | 10/2004 | Sherwood et al. |
| 6,883,516 | B2 | 4/2005 | Hindle et al. |
| 6,923,179 | B2 | 8/2005 | Gupta et al. |
| 7,040,314 | B2 | 5/2006 | Nguyen et al. |
| 7,077,130 | B2 | 7/2006 | Nichols et al. |
| 7,117,867 | B2 | 10/2006 | Cox et al. |
| 7,128,067 | B2 | 10/2006 | Byron et al. |
| 7,147,170 | B2 | 12/2006 | Nguyen et al. |
| 7,159,507 | B2 | 1/2007 | Grollimund et al. |
| 7,163,014 | B2 | 1/2007 | Nichols et al. |
| 7,167,776 | B2 | 1/2007 | Maharajh et al. |
| 7,173,222 | B2 | 2/2007 | Cox et al. |
| 7,351,684 | B2 | 4/2008 | Tichy et al. |
| 7,367,334 | B2 | 5/2008 | Faison, Jr. et al. |
| 7,373,938 | B2 | 5/2008 | Nichols et al. |
| 7,400,940 | B2 | 7/2008 | McRae et al. |
| 7,473,675 | B2 | 1/2009 | Tichy et al. |
| 7,500,479 | B2 | 3/2009 | Nichols et al. |
| 7,534,756 | B2 | 5/2009 | Tichy et al. |
| 7,743,766 | B2 | 6/2010 | Gupta et al. |
| 8,034,759 | B2 | 10/2011 | Man et al. |
| 8,110,538 | B2 | 2/2012 | Martin et al. |
| 8,442,390 | B2 | 5/2013 | Nichols et al. |
| 8,696,986 | B2 | 4/2014 | Rovison, Jr. et al. |
| 8,716,339 | B2 | 5/2014 | Larson et al. |
| 8,772,218 | B2 | 7/2014 | Cunningham et al. |
| 8,789,716 | B2 | 7/2014 | Larson et al. |
| 8,987,331 | B2 | 3/2015 | Larson et al. |
| 9,044,403 | B2 | 6/2015 | Shultz |
| 9,050,384 | B2 | 6/2015 | Grant et al. |
| 9,061,300 | B2 | 6/2015 | Belcastro et al. |
| 9,192,909 | B2 | 11/2015 | Kraus et al. |
| 9,241,483 | B2 | 1/2016 | Golden et al. |
| 2004/0120844 | A1 | 6/2004 | Tribelsky et al. |
| 2005/0238631 | A1 | 10/2005 | Burwell |
| 2007/0262478 | A1 | 11/2007 | Price et al. |
| 2008/0000931 | A1 | 1/2008 | Tichy et al. |
| 2009/0246336 | A1 | 10/2009 | Burnett et al. |
| 2013/0199539 | A1 | 8/2013 | Webster |
| 2014/0178249 | A1 | 6/2014 | Tichy et al. |
| 2014/0238445 | A1* | 8/2014 | Stokes ............... C11D 3/48 134/28 |
| 2014/0275267 | A1 | 9/2014 | Beug-Deeb et al. |
| 2014/0328949 | A1 | 11/2014 | Adams et al. |
| 2014/0378544 | A1 | 12/2014 | Kraus et al. |
| 2015/0102061 | A1 | 4/2015 | Larson et al. |
| 2015/0297770 | A1 | 10/2015 | Larson et al. |
| 2016/0022850 | A1 | 1/2016 | Tsai et al. |

FOREIGN PATENT DOCUMENTS

| | | |
|---|---|---|
| WO | 01/28511 A2 | 4/2001 |
| WO | 01/34211 A2 | 5/2001 |
| WO | 2010/056871 A2 | 5/2010 |
| WO | 2011/139300 A2 | 11/2011 |
| WO | 2015/074144 A1 | 5/2015 |

OTHER PUBLICATIONS

Pavliv, L, et al., "Formulation and Manufacturing", Drug and Biological Development : From Molecule to Product and Beyond, Ronald Evens, editor, Springer US, publisher, p. 210, 2007 (1 page).
Zhao, Xuebing, et al., "Preparation of Peracetic Acid from Acetic Acid and Hydrogen Peroxide : Experimentation and Modeling", The Chinese Journal of Process Engineering, vol. 8, No. 1, Feb. 2008 (7 pages).
Rutala, William, et al., "Guideline for Disinfection and Sterilization in Healthcare Facilities, 2008", Center for Disease Control, Dept. of Health and Human Services, USA, pp. 7-30 and 50-51, 2008, (158 pages).
"Acute Exposure Guideline Levels for Selected Airborne Chemicals", Committee on Acute Exposure Guideline Levels, Committee on Toxicology, & Board on Environmental Studies and Toxicology, National Research Council of the National Academies, The National Academies Press, Washington, D.C., vol. 8, Chapter 7, 2010, pp. 327-367, (41 pages).
Nyamunda, B. C., et al., "Hydrogen Peroxide as an Oxidant for Organic Reactions", Journal of Atoms and Molecules, vol. 3, No. 1, Feb. 2013 (23 pages).
"Common Chemicals Used for Cleaning and Decontamination Guideline", Department of Environmental Health and Safety, University of Colorado, Aug. 2014, (3 pages).
International Search Report and the Written Opinion of the International Searching Authority, dated Jul. 24, 2017, for corresponding application No. PCT/US2017/034519, filed May 25, 2017 (15 pages).

* cited by examiner

METHODS FOR DISINFECTION

CROSS-REFERENCE TO RELATED APPLICATIONS

This application claims the benefit of U.S. Provisional Patent Application 62/341,799, filed May 26, 2016.

FIELD OF THE INVENTION

The present invention is in the field of disinfection and sterilization methods.

BACKGROUND OF THE INVENTION

There is a need for an inexpensive, effective, yet safe and convenient method to minimize the microbial burden of objects we interact with. In addition, this method must not leave behind microbes with resistance to future treatment. This need is primarily evidenced by unacceptably high rates of infection in hospitals and health care facilities. But there are also problems in daycare facilities, schools, the food industry and the travel industry, among others. Additionally, these problems are becoming more severe as microbes which are resistant to virtually all known antibiotics are becoming more common. It has been predicted that we may soon enter a post-antibiotic era that will be similar to the pre-antibiotic era in which even minor infections will be life threatening.

Consequently, a method for killing virtually all microbes is needed that prevents the microbes from developing a resistance and with ingredient compounds that are not hazardous to humans, pets and other beneficial life that may be exposed to them. A potential way to do this would be to utilize ingredients and methods that are relatively safe to humans but are biocidal.

For centuries prior to the antibiotic era, humans had safely utilized natural biocides. Vinegar has been well known to protect foodstuffs from the effect of microbes, evidenced by many foods being pickled. Ethanol has also been used for years. In Europe, for example, medieval monks who brewed and drank wine or beer instead of the local water had much longer life spans. More recently, hydrogen peroxide has been shown to be used by animals as an internal method to ward off the microbes that infest them. Additionally, electricity has a biocidal effect, as does ultraviolet light.

The problem with these safe biocides is that each one individually is not effective against all types of microbes, and several target microbes have developed defense mechanisms against these biocides. However, combinations of two or more of these biocides have proven to work synergistically to enhance each one's effects. Particularly, combining hydrogen peroxide and acetic acid (the primary component of vinegar) to form peroxyacetic acid has proven to be especially effective. Several methods, apparatuses, and disinfecting systems utilizing peracids, including peroxyacetic acid, have been described in U.S. Pat. Nos. 6,692,694; 7,351,684; 7,473,675; 7,534,756; 8,110,538; 8,696,986; 8,716,339; 8,987,331; 9,044,403; 9,050,384; 9,192,909; 9,241,483; and U.S. Patent Publications 2015/0297770 and 2014/0178249, the disclosures of which are incorporated by reference in their entireties.

However, one of the biggest drawbacks with using peracids is that they are easily hydrolyzed to produce ordinary acids and either oxygen or water. Consequently, peroxyacetic acid has limited storage stability and a short shelf life. Peroxyacetic acid instability is described in detail in U.S. Pat. No. 8,034,759, the disclosure of which is incorporated by reference in its entirety. Often, commercially available products contain additional components to combat this problem, by including either a large excess of hydrogen peroxide to drive equilibrium toward the peracid form, or stabilizers such as other acids, oxidizing agents, and surfactants. Some methods have prevented degradation during shipping and storage by requiring that individual components of a peracid composition be mixed together, and subsequently applied, at the location and time that a target will be disinfected or sterilized. Yet, these methods nonetheless require expensive additives that are difficult to obtain, such as polyhydric alcohols, esters, and transition metals, as well as specific reaction conditions, in order to be effective. In all cases, the peracid is nonetheless formed in solution and then subsequently applied to areas or surfaces that need disinfecting.

Additionally, there are known safety concerns associated with dispersing airborne particles or peracids into the environment in an effort to sterilize or disinfect it. Particularly, inhaling peracids can be dangerous, especially at the micron-level particle sizes necessary to effectively disinfect a plurality of surfaces within common inhabitable areas such as hospital rooms, hotel rooms, bathrooms, lobbies, offices, and transportation cabins. Safety data and recommended exposure levels are described in detail in Acute Exposure Guideline Levels for Selected Airborne Chemicals, National Research Council (US) Committee on Acute Exposure Guideline Levels, pg. 327-367, Volume 8, 2010, the disclosure of which is hereby incorporated by reference in its entirety.

As a result, there is still a need for sterilization and disinfecting methods utilizing peracids that are simultaneously effective, convenient, and safe, while at the same time using cheap and readily available materials.

SUMMARY OF THE INVENTION

The present invention provides a method for disinfecting surfaces using peracid chemistry that eliminates instability issues and human safety issues associated with forming the peracid at any point prior to contacting a surface. The present invention provides improved methods for disinfecting surfaces by dispersing peracid reactant compounds in separate application steps and forming the peracid directly on the surface to be disinfected.

In one embodiment of the invention, a broad and complete microbe kill is achieved through careful selection of substantially different mechanisms acting in concert with each other, in order that no microbe can develop mutations that would render future generations resistant.

In another embodiment of the invention, a method of disinfecting a surface in need of disinfecting within an area is provided, comprising the steps of: a) dispersing into the area a multiplicity of droplets of a first aqueous composition comprising a first peracid reactant compound that is either hydrogen peroxide or an organic acid compound; b) allowing a time sufficient for the first aqueous composition to distribute throughout the area, and to deposit and coalesce into a layer upon the surface; c) dispersing into the area a multiplicity of droplets of a second aqueous composition comprising a second peracid reactant compound that is the other of the first peracid reactant compound; and d) allowing a second time sufficient for the droplets of the second aqueous composition to deposit onto the coalesced layer of the first aqueous composition to form a reaction layer, thereby forming a peracid in situ on the reaction layer and disinfecting the surface.

In another embodiment of the invention, the organic acid compound is acetic acid.

In another embodiment of the invention, the effective diameter of the multiplicity of droplets is controlled to be small enough to allow the droplets to reach a diversity of the intended surfaces to be disinfected within an area, and to be large enough to minimize deep lung penetration if the droplets were to be inhaled.

In another embodiment of the invention, the coalesced layer of the first aqueous composition has a substantially uniform thickness.

In another embodiment of the invention, a stoichiometric amount of the organic acid compound in the reaction layer is equal to or greater than a stoichiometric amount of the hydrogen peroxide compound in the reaction layer.

In another embodiment of the invention, a stoichiometric amount of the dispersed first aqueous composition comprising hydrogen peroxide is equal to or greater than a stoichiometric amount of the dispersed second aqueous composition comprising organic acid.

In another embodiment of the invention, the multiplicity of droplets of the second aqueous composition is electrostatically charged.

In another embodiment of the invention, the multiplicity of droplets of the second aqueous composition can be charged with the opposite polarity of the first aqueous composition.

In another embodiment of the invention, droplets of either aqueous composition can be dispersed using an electrostatic sprayer. The charge polarity of the sprayer when it sprays the first and the second peracid reactant compound can be optimized to provide the most desirable reaction of the first and second compounds.

In another embodiment of the invention, the surface in need of disinfecting is electrically grounded.

In another embodiment of the invention, either aqueous composition can further comprise a lower-chain alcohol, particularly ethanol, decreasing the surface tension of the dispersed droplets and providing enhanced biocidal activity to the peracid reactant compounds.

In another embodiment, the invention provides a method of disinfecting a surface, comprising the steps of a) spraying electrostatically a first aqueous composition comprising hydrogen peroxide, toward and into contact with the surface; b) spraying a second aqueous composition comprising an organic acid compound toward and into contact with the first aqueous composition on the surface; and c) allowing the second aqueous liquid composition to contact the first aqueous liquid composition to form a reaction layer, thereby forming a peracid in situ on the reaction layer and disinfecting the surface.

In a further embodiment, log-6 kills of microbes are achieved using individual ingredients that are food-safe.

DETAILED DESCRIPTION OF THE INVENTION

The present disclosure includes a method and a system for sterilizing rooms, areas, and surfaces within those areas, particularly by generating peracids on those targets in situ by applying peracid reactant compounds in two or more separate applications. The methods and system described herein have several advantages over conventional disinfecting systems utilizing peracids to kill microbial populations. The methods of the present invention do not require stabilizers for the peracid reactants because the peracid reactants are applied individually and the peracid is formed directly on the target surface after the reaction ingredients are added sequentially.

It should be understood that while reference is made to exemplary embodiments and specific language is used to describe them, no limitation of the scope of the invention is intended. Further modifications of the methods and system described herein, as well as additional applications of the principles of those inventions as described, which would occur to one skilled in the relevant art and having possession of this disclosure, are to be considered within the scope of this invention. Furthermore, unless defined otherwise, all technical and scientific terms used herein have the same meaning as commonly understood by one of ordinary skill in the art to which embodiments of this particular invention pertain. The terminology used is for the purpose of describing those embodiments only, and is not intended to be limiting unless specified as such.

Definitions

As used in this specification and in the claims, the singular forms "a," "an," and "the" include plural referents unless the content clearly dictates otherwise.

The term, "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Similarly, whether or not a claim is modified by the term, "about," the claims included equivalents to the quantities recited.

As used herein, the term, "aqueous composition," refers to a combination of liquid components that includes water. Most commonly, aqueous compositions are synonymous with the term "solution" as it is commonly used in the art for this invention. However, depending on the identity of components in the composition in addition to water, "aqueous compositions" can also encompass mixtures, emulsions, dispersions, suspensions or the like. Furthermore, while water must be present, it need not comprise the majority of the aqueous composition.

As used herein, the terms, "biocide" and "biocidal compound," refer to chemical substances intended to destroy, deter, render harmless, or exert a controlling effect on any organisms that are harmful to human or animal health or that cause damage to natural or manufactured products. Non-limiting examples of biocides include peroxides, organic acid compounds, peracids, and alcohols.

The term, "effective diameter," refers to either the geometric diameter of a spherical droplet, or of the distance from side-to-side of a distorted spherical droplet at the droplet's widest point, which has been dispersed into an area but before it deposits onto a surface to be disinfected.

As used herein, the phrase, "food processing surface" refers to a surface of a tool, a machine, equipment, a shipping container, railcar, structure, building, or the like that is employed as part of a food transportation, processing, preparation, or storage activity. Non-limiting examples of facilities within which food processing surfaces are utilized for food transportation, processing, preparation, or storage activities can include food or plant growing facilities housing items such as plants, produce, vegetables, or cannabis, or livestock animal stock yards handling animals or animal products from chicken, turkeys, eggs, hogs, or cattle. Examples of food processing surfaces can include surfaces of food processing or preparation equipment (e.g. slicing, canning, or transport equipment, including flumes), of food processing wares (e.g. utensils, dishware, wash ware, and bar glasses), of all agricultural products utilized in the production cultivation, or housing of food, and of floors, walls, or fixtures of structures in which food processing occurs. Food processing surfaces are found and employed in food anti-spoilage air circulation systems, aseptic packaging sanitizing, food refrigeration and cooler cleaners, and sanitizers, ware washing sanitizing, blancher cleaning and sanitizing, food packaging materials, cutting board additives, third-sink sanitizing, beverage chillers and warmers, meat chilling or scalding waters, auto-dish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition that is edible with or without further preparation. Food products include meat (e.g. red meat and pork), seafood, poultry, produce (e.g. fruits and vegetables), eggs, living eggs, egg products, ready-to-eat food, wheat, seeds, roots, tubers, leaves, stems, corns, flowers, sprouts, seasonings, or a combination thereof. The term, "produce," refers to food products such as fruits and vegetables and plants or plant-derived materials that are typically sold uncooked and, often, unpackaged, and that can sometimes be eaten raw.

The terms, "free" or "substantially free" refers to the total absence or near total absence of a particular compound in a composition, mixture, or ingredient.

The term, "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term, "instrument," refers to the various medical or dental instruments or devices that can benefit from cleaning with a composition according to the present invention. As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the phrase, "organic acid compound," refers to any organic acid that is capable of forming a peracid that is effective as a disinfecting agent.

As used herein, the terms, "peracid" or "peroxy acid" refer to any acid having the hydrogen of a hydroxyl group replaced by a perhydroxyl group. Oxidizing peracids are referred herein as peroxycarboxylic acids.

As used herein, the phrase, "peracid reactant compound" refers to a reactant compound that will react to form a peracid.

As used herein, the term, "peroxide compound," refers to any compound that can react with an organic acid to form a peracid, including but not limited to hydrogen peroxide, metal peroxides, and ozone.

As used herein, the term, "reaction layer," refers to the layer formed on a surface to be disinfected when a multiplicity of droplets including a second peracid reactant compound is deposited onto the coalesced layer of the multiplicity of droplets including a first peracid reactant compound. Peracids are formed in situ on the reaction later and disinfect the surface.

The term, "weight percent," "percent by weight," "w/w," and other variations, as used herein, refer to the concentration of a substance as a weight of that substance divided by the total weight of the composition, multiplied by 100. It is understood that "percent," "%," and like terms are intended to be synonymous with "weight percent," "percent by weight," etc, rather than percent by volume of the composition, unless otherwise indicated.

In describing embodiments of the disinfecting methods and system in the present disclosure, reference will be made to "first" or "second" as they refer to aqueous compositions or peracid reactant compounds. Except when there is clear context that a specific order is intended, "first" and "second"

are merely relative terms, and a "first" composition or reactant compound described could just as easily and conveniently be referred to as a "second" composition or reactant compound, and such description is implicitly included herein.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 0.5% to about 10% by weight includes not only the explicitly recited limits of 0.5% by weight and 10% by weight, but also individual weights such as 1% by weight and 5% by weight, and sub-ranges such as 2% to 8% by weight, 5% to 7% by weight, etc.

Embodiments of the Invention

In accordance with these definitions, the present invention provides several methods for disinfecting target surfaces within an area by forming a peracid on those surfaces in situ. The potential applications for these methods can be diverse, including but not limited to disinfecting food products and processing surfaces, health care surfaces and instruments, laboratories, restrooms, vehicles, schools, offices, public transportation, industrial facilities, and countless other areas and surfaces. This invention overcomes the deficiencies associated with forming peracids prior to applying them for sterilization, particularly with regard to the instability and safety of the peracid in solution.

While other sterilization methods attempt to solve this problem by including one or more additives in the reaction mixtures to promote the retention of the peracid in the system, many of these additives are expensive to produce and are not readily attainable for an average person with no connection to the chemical industry. Furthermore, many stabilizers are difficult to volatilize and can sometimes undesirably discolor the disinfected surfaces as they are treated or leave behind a film on those surface. In some instances, the discoloration or the film that is left behind cannot be subsequently removed. In contrast, the present invention harnesses the power of peracid chemistry to disinfect target surfaces while utilizing ingredients that have a very long shelf life and that are generally regarded as safe for handling and can be obtained at one's local grocery and department stores. The ingredients are easy to volatilize and can evaporate from treated surfaces without harming the surfaces or leaving behind any permanent discolorations, residues, or films.

Without being limited by theory, it is believed that peracids are so effective as disinfectants because they are powerful oxidizing agents that can irreversibly damage proteins and DNA within microorganisms. Peracids are formed in an acid-catalyzed reaction when a strong oxidizing agent, such as a peroxide compound, comes into contact with an organic acid compound. For example, in a system that utilizes acetic acid as the organic acid compound, addition of a peroxide compound such as hydrogen peroxide can result in a reaction in which peracetic acid and water are produced in equilibrium as shown below:

Once the peracid is formed on the surface to be disinfected, it is strongly electrophilic. If there are no electron-rich sources in solution with the peracid, the excess water will drive equilibrium toward hydrolysis of the peracid and back into production of the parent acid. Additionally, as the parent acid becomes increasingly acidic, the resultant peracid similarly becomes more reactive. Thus, even though the resultant peracid could become an even better disinfectant under those conditions, it is also more unstable and likely to never reach the target surface, regardless of how immediately before application the individual components are mixed. Consequently, embodiments of this invention can be more effective than the present art, especially in industrial applications where stronger and more strictly-controlled components can be used, because the peracid is formed in situ on the target surface, disinfecting the surface before the peracid can hydrolyze and revert back to the parent acid.

In a first embodiment of this invention, a method is provided to disinfect surfaces within an area that needs disinfecting, comprising the steps of: dispersing into the area a multiplicity of droplets of a first aqueous composition comprising a first peracid reactant compound that is either hydrogen peroxide or an organic acid; allowing a time sufficient for the first aqueous composition to distribute throughout the area, and to deposit and coalesce into a layer upon the surface; dispersing into the area a multiplicity of droplets of a second aqueous composition comprising a second peracid reactant compound that is the other of the first peracid reactant compound; and allowing a second time sufficient for the droplets of the second aqueous composition to deposit onto the coalesced layer of the first aqueous composition to form a reaction layer, thereby forming a peracid in situ in the reaction layer and disinfecting the surface.

Since a peracid is formed only on the surface to be disinfected, the effectiveness of the method is generally independent of the order in which the peracid reactant compounds are dispersed. Thus, the first peracid reactant compound can either be an organic acid compound or a peroxide compound, so long as the second peracid reactant compound is the opposite compound of that chosen to be the first peracid reactant compound. For example, the second peracid reactant compound would be an organic acid compound if a peroxide compound was selected to be the first peracid reactant compound, and vice versa. Although the compositions containing the peracid reactant compounds are generally mostly aqueous, water need not comprise the majority of the composition. Furthermore, any liquid carrier system that can facilitate the formation of the peracid from a peroxide compound and an organic acid compound can be used.

The peroxide compound present in either aqueous composition is any compound that can react with an organic acid to form a peracid. Generally, these will include but not be limited to hydrogen peroxide, metal peroxides, or ozone. In some embodiments of the invention, the peroxide compound is hydrogen peroxide. Typically, an aqueous composition containing a peroxide compound comprises at least about 0.1% by weight of the peroxide compound and up to about 25% by weight of the peroxide compound. More typically, the aqueous composition comprises at least about 1% by weight of the peroxide compound and up to about 10% by weight of the peroxide compound. Even more particularly, the aqueous composition comprises at least about 3% by weight of the peroxide compound up to about 7% by weight of the peroxide compound.

The organic acid compound present in either aqueous composition is any organic acid that can effectively form a peracid by reacting with a peroxide compound. Generally, these will include but not be limited to carboxylic acids. Non-limiting examples of acids which can be used include formic acid, acetic acid, citric acid, oxalic acid, propanoic acid, lactic acid, butanoic acid, pentanoic acid, octanoic acid, and mixtures thereof. In some embodiments of the invention, the organic acid compound is acetic acid. Typically, an aqueous composition containing an organic acid compound comprises at least about 0.5% by weight of the organic acid compound and up to about 50% by weight of the organic acid compound. More typically, the aqueous composition comprises at least about 2% by weight of the organic acid compound and up to about 20% by weight of the organic acid compound. Even more particularly, the aqueous composition comprises at least about 5% by weight of the organic acid compound up to about 10% by weight of the organic acid compound.

The time sufficient for the multiplicity of droplets of each of the aqueous compositions to disperse into an area, and to deposit and coalesce into a layer upon the surface or surfaces to be disinfected, can depend on several factors, including but not limited to: the size of the droplets as they are dispersed; the velocity and direction of the droplets as they are dispersed; the size and humidity of the area; and the identity and concentration of the components within the aqueous composition. With regard to droplet size, the time sufficient for the droplets to reach and coalesce upon the surfaces to be disinfected is roughly inversely proportional to the size of the droplet. Without being bound by any particular theory, when a droplet is small, with an effective diameter of about 1 to about 2 microns, more time is needed to deposit onto a surface than when the droplet is large, with an effective diameter of about 50 to about 100 microns, because smaller droplets are less affected by gravity before they deposit onto the target surface. Although these large droplet sizes are functionally adequate for disinfecting multiple surfaces in larger areas such as rooms or shipping containers, it has been observed that the ability of the droplets to remain in the air long enough to overcome gravity and reach the surfaces to be disinfected becomes compromised once the effective diameter of the droplets reaches about 20 microns or more.

However, issues can also potentially arise when the effective diameter of the droplets is small. It is known that airborne droplets can be inhaled and retained in the deep lung at effective diameters less than about eight to about ten microns, as illustrated in Drug and Biological Development: From Molecule to Product and Beyond, edited by Ronald Evens, pg. 210 and applicable sections, 2007, hereby incorporated by reference in its entirety. Consequently, in some embodiments of the invention where a person is present in the area while either aqueous composition is dispersed in droplet form, the effective diameter of a preponderance of the droplets should remain above about 10 microns in order to avoid deep lung penetration.

In some embodiments of the invention, once the multiplicity of droplets of the first aqueous composition is deposited onto a surface to be disinfected, the droplets must coalesce into a layer with a substantially uniform thickness in order to provide maximal coverage on the surface. In preferred embodiments, the thickness of the coalesced layer should be minimized while also substantially covering all exposed and unexposed locations on the surface. The thickness of the coalesced layer is dependent on both the size and surface tension of the multiplicity of droplets. In some embodiments where the multiplicity of droplets consists only of peroxide compounds or organic acid compounds in an aqueous solution, the droplets would possess a surface tension close to that of pure water, which is about 72 dyn/cm at 20° C. In this situation, the coalesced layer may be thicker because the droplets will narrowly spread after being deposited upon the surface. Thus, more composition is needed to completely cover and disinfect the entire surface. Conversely, the multiplicity of droplets may additionally include non-aqueous compounds that lower a composition's surface tension. For example, pure ethanol has a surface tension of about 22.27 dyn/cm at 20° C., and aqueous solutions containing ethanol exhibit a reduced surface tension relative to the surface tension of pure water. In this situation, the composition droplets with the lower surface tension will more widely spread, creating a thinner coalesced layer that requires less of the composition to completely cover and disinfect the surface. Based on the functional droplet sizes discussed above, in some embodiments, the coalesced layer can have a substantially uniform thickness of about 1 micron to about 20 microns; particularly, the coalesced layer can have a substantially uniform thickness of about 2 microns to about 8 microns.

In some embodiments, an alcohol can be added to one or both of the aqueous compositions to decrease the surface tension of the compositions and the droplets deposited on the surface to be disinfected. The alcohol contained in either aqueous composition promotes a thinner coalesced layer without having to reduce the droplet size to a smaller effective diameter. Furthermore, an alcohol also independently provides biocidal activity separate from the peracid. Therefore, using alcohols in combination with forming the peracid in situ on the surface to be disinfected may provide a synergistic effect in the antimicrobial activity seen from the peracid alone.

Although an alcohol in liquid form can be used at high concentrations (70% by weight or above) to sterilize instruments or surfaces, many alcohols are combustible at those same concentrations when volatilized, especially as the temperature is increased in the ambient environment or the area immediately surrounding the dispersing device. Thus, a typical aqueous composition containing ethanol comprises at least about 1% by weight of ethanol and up to about 25% by weight of ethanol. Even more particularly, the aqueous composition comprises at least about 10% by weight of the alcohol to about 20% by weight of the alcohol.

The alcohol present in an aqueous composition can be a single alcohol or a combination of multiple alcohols. The alcohol can include aliphatic alcohols and lower-chain alcohols. As used herein, the term, "lower-chain alcohol" describes an alcohol having 1, 2, 3, or 4 carbons. The alcohol can be selected from a straight-chained, saturated, substituted, or other carbon-containing alcohols, including branched aliphatic alcohols, alicyclic alcohols, and unsaturated alcohols. For practical considerations, lower-chain alcohols such as methanol, ethanol, isopropanol, t-butanol, and denatured alcohols can be used because of their properties and cost. The alcohol can be selected to satisfy the requirements for food-grade and food-safe systems. In some embodiments, aqueous compositions that include an alcohol can comprise ethanol.

An advantage of the components described above, including the peracid reactant compounds and alcohols, is that they have been chosen because they can be readily volatilized after the sterilization is complete. In embodiments where the coalesced layer on the surfaces to be disinfected is about 1 micron to about 20 microns, the aqueous compositions may rapidly evaporate from treated surfaces, obviating the need for additional treatments to remove unwanted components and waste products, and facilitating a faster turnover of the area in which the surfaces are located.

In another embodiment of the invention, the multiplicity of droplets of either aqueous composition may be electrostatically-charged. An example of electrostatic spraying of a solution is described in U.S. Pat. No. 6,692,694, the disclosure of which is incorporated by reference in its entirety. FIG. 1 illustrates an example of a commercial electrostatic spray device 10 according to the prior art. Electrostatic spray device 10 includes a housing 12; a container 14 associated with the housing 12 for storing a liquid; multiple nozzles 16 in liquid communication with the container 14 for dispensing aerosolized droplets of the liquid; and a high capacity charging system 18 capable of imparting an electrostatic charge on the droplets after they are dispersed.

There are several advantages that can be exploited by dispersing the droplets with an electrostatic charge, including but not limited to: a more effective and targeted dispersal onto surfaces to be disinfected; application onto non-line-of-sight vertical and under-side surfaces; enhanced activation, or alternatively, stabilization, of the peracid reactant compounds prior to the formation of the peracid on the surface. Without being limited by theory, it is believed that applying an electrostatic charge leads to a more effective dispersal of the aqueous composition because the multiplicity of like-charged droplets repel each other according to Coulomb's law. As shown in FIG. 2, negatively charged particles 120 dispensed from the nozzle of an electrostatic spray device 116 deposit onto all faces of a positive or neutrally-charged surface 130. Droplets of a like-charge additionally are likely to distribute evenly across an area and deposit onto a diversity of surfaces, including the back surfaces and underside surfaces of an object, in an effort to maximize the distance between like charges on adjacent droplets.

Because of the volume of the aqueous composition dispersed in the area, the like-charged particles can spontaneously coalesce into a layer on the surface. In some embodiments, the first aqueous composition is electrostatically charged to provide a uniform distribution of droplets in a continuous coalesced layer on the surfaces to be disinfected, followed by dispersing the second aqueous composition into the area. In other embodiments, Coulomb's law can be further exploited by electrostatically charging the multiplicity of droplets of the second aqueous composition, including with the opposite polarity as the multiplicity of droplets of the first aqueous composition, creating an attraction between the first aqueous composition and the second aqueous composition, and enhancing the contact of the peracid reactant compounds with each other in the coalesced layer on the surface to be disinfected.

Additionally, the electrostatic charge placed on an aqueous composition can be selected to enhance the reactivity of the peracid reactant compounds. Without being bound by any one theory, dispersing aqueous compositions comprising hydrogen peroxide with a negative electrostatic charge supplies each droplet with solvated electrons that can cause conversion of hydrogen peroxide to two hydroxyl radicals. Upon contact with an organic acid, the presence of hydroxyl radicals can enhance the formation of the peracid, as well as the subsequent disinfecting of the target surface.

In some embodiments, the aqueous composition that includes the peroxide compound may be electrosprayed with a negative charge, while the aqueous composition including the organic acid compound may be electrosprayed with a positive charge. In other embodiments, the opposite situation may occur in which the aqueous composition including the peroxide compound may be electrosprayed with a positive charge, and the aqueous composition including the organic acid compound may be sprayed with a negative charge. Ultimately, any combination of electrostatic charge (positive, negative, or neutral) may be applied to either the first or second aqueous composition or both, independently of the identity of the components present in either aqueous composition.

In addition to augmenting the deposition of the aqueous compositions on the surfaces to be disinfected and enhancing the peracid-forming reaction, utilizing electrospray brings additional supplemental benefits to the methods described herein. While the attraction that the electrostatically-charged droplets have for surfaces is beneficial for facilitating the reaction on the surfaces to be disinfected, it also provides an additional safety measure for any persons who may be in the area. Smaller droplets that would otherwise penetrate into someone's deep lung would instead be attracted to the surfaces of the person's nasal cavity or mouth, where their effects, if any, can be easily neutralized by the body. Additionally, the repulsion experienced by identically-charged particles can cause droplets to remain in the air for a longer period of time without being forced to the ground by gravity. Thus, larger droplet sizes can be used and disinfection of surfaces within larger areas is facilitated.

In some embodiments, surfaces within the area can also be electrically grounded prior to dispersing the first aqueous composition by electrostatic spray. Because an electric attraction is created between the grounded surfaces and the charged droplets in the area, the droplets can become attracted only to the grounded surfaces. As a non-limiting example, high-traffic or highly-contaminated surfaces in a hospital room such as door handles, faucets, and hospital bedrails and bars, can be quickly targeted by grounding them prior to disinfecting, facilitating a faster turnover of the room between patients. In other embodiments, surfaces that are already ground within an area can be removed from the ground source prior to dispersing an electrostatically-charged first aqueous composition, in order to provide a better blanket coverage of all surfaces within the area. In further embodiments, electrostatically spraying selected grounded surfaces with the first aqueous composition can be utilized in combination with dispersing a second aqueous composition with no electrostatic charge in order to provide general surface coverage throughout the area. In some embodiments, an electrostatic charge may be applied either prior to the aerosolization of the aqueous composition or after the composition has been dispersed. Distribution of the multiplicity of electrostatically-charged droplets can be tailored by adjusting the magnitude of the voltage applied to the nozzle on the electrostatic sprayer, nozzle size or type, and the flow rate of the aqueous composition through the nozzle.

Delivery of the peracid reactant compounds in aqueous compositions can be made by methods in addition to electrospraying the surfaces to be disinfected, especially where those surfaces are inside air ducts, confined spaces, or in very large areas. In these situations, vaporizing the aqueous compositions in the ambient air or introducing them into a hot gaseous stream may be highly effective. Sterilization using these methods has been described in U.S. Pat. Nos. 8,696,986 and 9,050,384, the disclosures of which are incorporated by reference in their entireties. Similar to the other patent references described above, the methods described in these patents require that the peracid be formed and then dispensed into an area. In contrast, peracid reactant compounds are dispersed in separate application steps, thereby forming the peracid in situ only on the surfaces to be disinfected. Other dispersal methods and systems known to those skilled in the art can similarly be modified and utilized to practice the methods of the present invention, provided that aqueous compositions containing peracid reactant compounds are applied or dispersed sequentially and peracid is formed in situ on the surface to be disinfected.

In some embodiments of the invention, the disinfectant methods described above for generating peracids on surfaces to be disinfected can be used for a variety of user-identified biocidal purposes, including antimicrobial, bleaching, or sanitizing applications. In other aspects, the generated peracids may be used to kill one or more of the food-borne pathogenic bacteria associated with a food product, including, but not limited to *Salmonella typhimurium, Campylobacter jejuni, Listeria monocytogenes*, and *Escherichia coli* 0157:H7, yeast, and mold.

Figure 1:
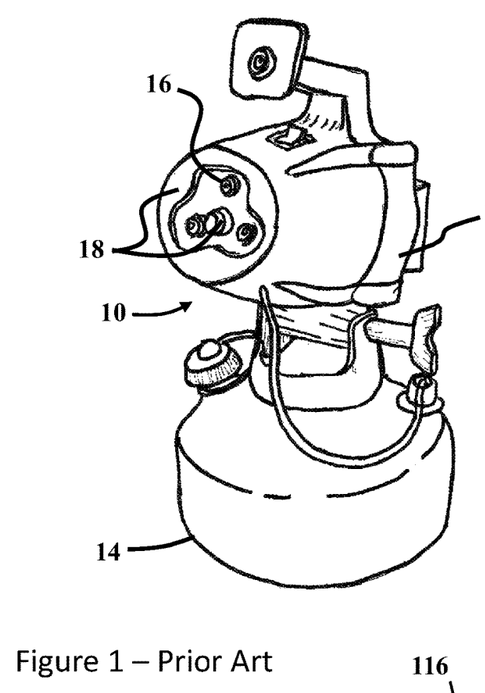
FIG. 1 shows a photograph of the commercial electrospray device according to the prior art.
Figure 2:
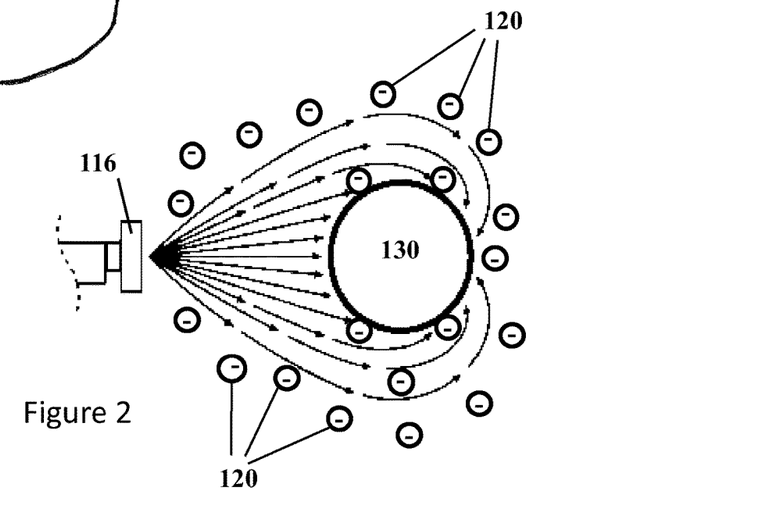
FIG. 2 shows the dispersion and distribution of identically electrostatically-charged droplets onto a surface in need of disinfecting.
Figure 3:
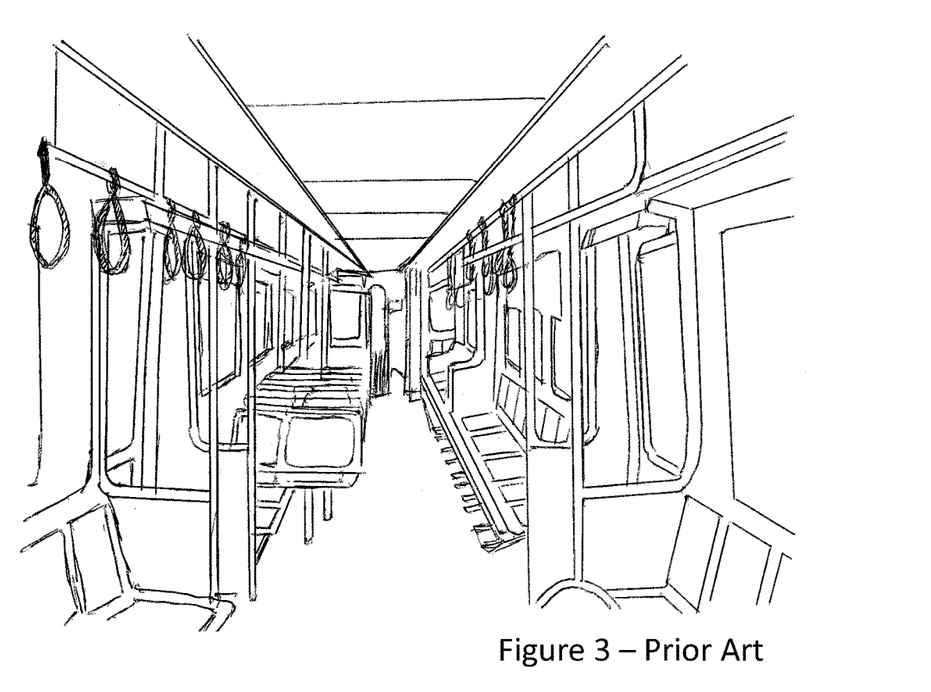
FIG. 3 shows a photograph of the interior of a passenger compartment of a train.
Figure 4:
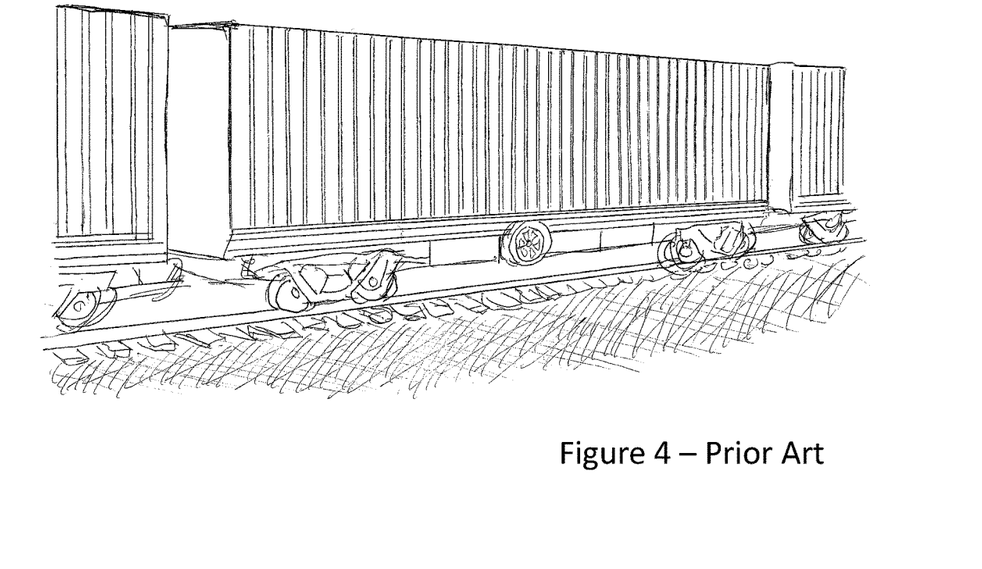
FIG. 4 shows a photograph of the exterior of a metal shipping container.
Figure 5:
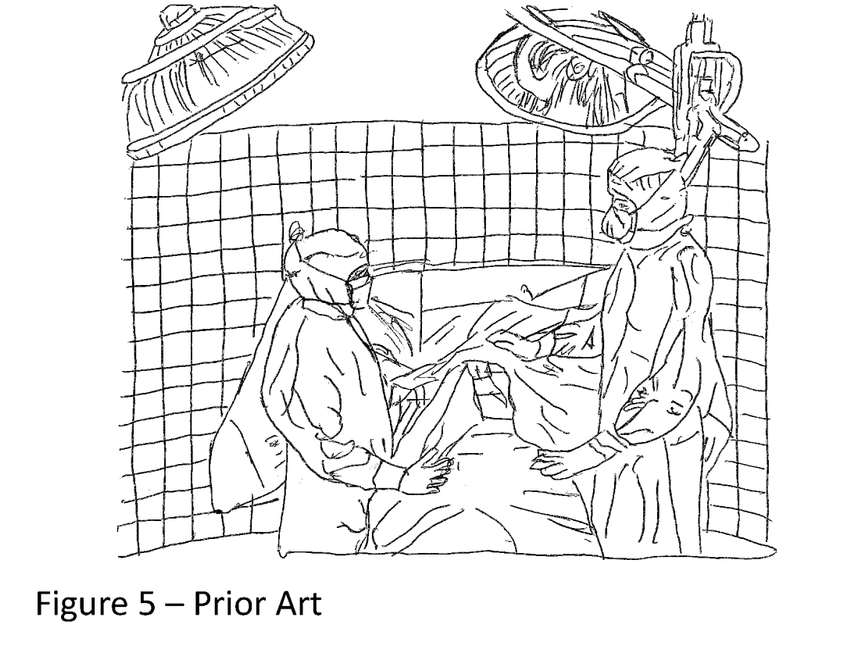
FIG. 5 shows a sketch of a sterile environment in an operating room.

In some embodiments, the peracids generated according to the methods of the present invention are effective for killing one or more of the pathogenic bacteria associated with a health care surfaces and instruments including, but not limited to, *Salmonella typhimurium, Staphylococcus aureus, Salmonella choleraesurus, Pseudomonas aeruginosa, Escherichia coli, Mycobacteria*, yeast, and mold. In other embodiments, the generated peracids are also effective in domestic or industrial applications and can be applied in a variety of areas including, but not limited to, passenger compartments in public transportation (FIG. 3), inside and outside surfaces of metal shipping containers (FIG. 4), operating rooms (FIG. 5), hospital patient rooms (FIG. 6), kitchens, bathrooms, factories, hospitals, dental offices, restaurants, laundry or textile services, and food processing plants.

Figure 6:
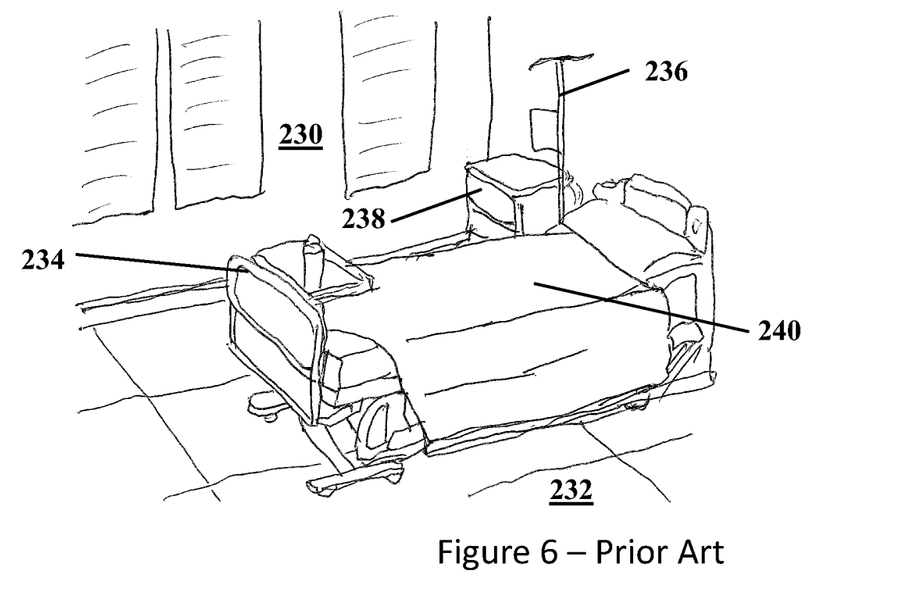
FIG. 6 shows a sketch of potential surfaces to disinfect in hospital patient room.

Additionally, compositions containing peracid reactant compounds can be applied to a variety of hard or soft surfaces having smooth, irregular, or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example, paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. FIG. 6 particularly illustrates the variety of surfaces in a hospital patient room that can be disinfected and sterilized, including wall 230, floor 232, bed frame 234, patient care equipment 236, bedside table 238, and bedding 240.

Furthermore, the peracids generated according to the methods and system of the present invention are effective against a wide variety of microorganisms, such as Gram-positive organisms (*Listeria monocytogenes* or *Staphylococcus aureus*), Gram-negative organisms (*Escherichia coli* or *Pseudomonas aeruginosa*), catalase-positive organisms (*Micrococcus luteus* or *Staphylococcus epidermidis*), or sporulent organisms (*Bacillus subtilis*).

In some embodiments of the invention, the methods can be practiced using solely food-grade components. For example, though not required, the disinfectant methods in this invention can be practiced substantially free of ingredients commonly present in many commercially available surface cleaners. Examples of non-food grade components that are often present in commercially available surface cleaners include, but are not limited to, aldehydes such as glutaraldehyde, chlorine- and bromine containing components, iodophore-containing components, phenolic-containing components, quaternary ammonium-containing components, and others. Furthermore, because peracids are formed in situ on the surface to be disinfected, heavy transition metals, surfactants, or other stabilizing compounds that could be used to prevent hydrolysis of the peracid prior to disinfecting the target surface are also not necessary and can be omitted from the aqueous compositions.

Accordingly, the methods to produce peracids directly on surfaces to be disinfected can be employed on foods and plant species to reduce surface microbial populations, or at manufacturing, processing, or transportation sites handling such foods and plant species. For example, the compositions can be used on food transport lines (e.g., as belt sprays); boot and hand wash dip-pans; food storage facilities; shipping containers; railcars; anti-spoilage air circulation systems; refrigeration and cooler equipment; beverage chillers and warmers, blanchers, cutting boards, third sink areas, and meat chillers or scalding devices.

While particular embodiments of the invention have been described, the invention can be further modified within the spirit and scope of this disclosure. Those skilled in the art will recognize, or be able to ascertain using no more than routine experimentation, numerous equivalents to the specific procedures, embodiments, claims, and examples described herein. As such, such equivalents are considered to be within the scope of the invention, and this application is therefore intended to cover any variations, uses or adaptations of the invention using its general principles. Further, the invention is intended to cover such departures from the present disclosure as come within known or customary practice in the art to which this invention pertains and which fall within the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references, patents, and patent applications mentioned in this specification are hereby incorporated by reference, and shall not be construed as an admission that such reference is available as prior art to the present invention. All of the incorporated publications and patent applications in this specification are indicative of the level of ordinary skill in the art to which this invention pertains, and are incorporated to the same extent as if each individual publication or patent application was specifically indicated and individually indicated by reference. The invention is further illustrated by the following working and prophetic examples, neither of which should be construed as limiting the invention. Additionally, to the extent that section headings are used, they should not be construed as necessarily limiting. Any use of the past tense to describe an example otherwise indicated as constructive or prophetic is not intended to reflect that the constructive or prophetic example has actually been carried out.

Working Examples

The following examples illustrate the embodiments of the invention that are presently best known. However, it is to be understood that the following are only exemplary or illustrative of the application of the principles of the present invention.

Numerous modifications and alternative compositions, methods, and systems may be devised by those skilled in the art without departing from the spirit and scope of the present invention. Thus, while the present invention has been described above with particularity, the following examples provide further detail in connection with what are presently deemed to be the most practical and preferred embodiments of the invention.

Example 1: Electrospray Distribution Study

A study was conducted in accordance with embodiments of the present disclosure to evaluate the distribution of an aqueous composition containing 5% by weight acetic acid onto multiple target surfaces using an electrostatic spray device. The electrostatic spray device used was a Hurricane ES™ Portable Electrostatic Aerosol Applicator. Two analytical balances were placed inside a 1 cubic meter, transparent glove box and connected to a computer station configured to collect and record mass measurements as a function of time. Each balance had a standard reading error of 0.005 grams. On each balance, a 1000 square centimeter plastic sheet was placed on a weighing pan. The position of each balance was staggered to be in different positions along the x, y, and z axes in relation to the electrostatic sprayer, placed at one end of the glove box.

The acetic acid composition was then electrosprayed throughout the entire glove box for 30 seconds with a set particle size of about 15 microns. The time of application was selected to provide a 2-micron thick coating within the treatment space as measured by the balances. During the application, mass measurements from the two balances were collected and recorded by the computer. The result of the test is provided as follows:

TABLE 1

| Electrospray Distribution | |
|---|---|
| | Mass - First Aqueous Composition (g) |
| Balance A (with 1000 cm² plate) | 0.205 +/− .005 |
| Balance B (with 1000 cm² plate) | 0.190 +/− .005 |

The mass of the first aqueous composition deposited on balance A and balance B indicated a difference of 0.015+/−0.010 grams. In combination with a qualitative observation that the inside surfaces of the glove box appeared to be equally coated with the acetic acid solution, it is believed that the electrospray method evenly distributed the first aqueous composition within the glove box.

Example 2: Preparation of First and Second Aqueous Compositions

Two separate aqueous compositions containing a peracid reactant compound, one containing acetic acid and one containing hydrogen peroxide, were prepared in accordance with embodiments of the present disclosure, which includes the following ingredients in approximate amounts.

First Aqueous Composition:
8% (w/w) Acetic Acid
15% (w/w) Ethanol
77% (w/w) Distilled Water
Second Aqueous Composition:
5% (w/w) Hydrogen Peroxide
15% (w/w) Ethanol
80% (w/w) Distilled Water The first aqueous composition and second aqueous composition were placed in separate containers until they could be dispersed on to surfaces in need of disinfecting within an area.

Example 3: Closed-System Log-Kill Studies by Sequential Addition of the Aqueous Compositions of Example 2

A study was conducted in accordance with embodiments of the present disclosure to determine the antimicrobial activity against common strains of bacteria by sequentially applying the two aqueous compositions of Example 2 to form peracids in situ directly on surfaces to be disinfected within a closed system. Cultures from commercially-available strains of four species of bacteria—*Bacillus subtilis, Micrococcus luteus, Rhodospirillum rubrum*, and *Staphylococcus epidermis*—were selected for a log-kill study because they possess several known defense mechanisms to common biocides while at the same time having different physical properties from each other. Sterilized, pre-poured agar plates were used as growth media to produce colonies of each bacteria. 8 plates were inoculated for each species. Of those 8 plates, 4 plates were exposed to the sequential application of the two aqueous compositions of Example 2, and 4 plates were held out as controls. Plates were inoculated using the standard T-method of streaking for log-kill studies, where the concentration of bacteria in the fourth quadrant of the plate is about 1,000,000× diluted with respect to the first quadrant. The test plates for each species were then placed inside the glove box with the lids open. Control plates were sealed with tape.

Upon closing the glove box, a multiplicity of droplets of the first aqueous composition was electrostatically applied to the entire glove box using a Hurricane ES™ Portable Electrostatic Aerosol Applicator. Droplets were sprayed for 20 seconds, using a flow rate of 1.7 oz/min, which correlates with a droplet size between about 5 and about 15 microns, according to the instructions provided by the manufacturer of the Hurricane ES™ applicator. The timing of the application of the first aqueous composition was selected to provide a coating having a calculated 2.5-micron thickness on the plates within the treatment space, as determined by the mass of the solution. About 1 minute after completing the spraying of the first aqueous composition, the second aqueous composition was sprayed for 3 seconds at a distance of about 6-8 inches using a hand sprayer, and the entire system was untouched for another 5 minutes. After evacuating the airspace of residual spray, the test plates were closed with their lids inside the glove box before being brought out into the ambient environment, where they were sealed with tape. During the transfer from the glove box to the outside environment, the lids of the *B. subtilis* test plates 1 and 2 were inadvertently opened. These plates were immediately closed and sealed with tape. All of the sealed test and control plates were then incubated at about 28° C. and inspected after 1, 2, and 4 days.

The results of the tests are provided as follows:

TABLE 2

Presence of colonies after 1 day (+ or −)

| Plate Number | B. subtilis | M. luteus | R. rubrum | S. epidermis |
|---|---|---|---|---|
| 1 | + | − | − | − |
| 2 | + | − | − | − |
| 3 | − | − | − | − |
| 4 | − | − | − | − |

TABLE 3

Presence of colonies after 2 days (+ or −)

| Plate Number | B. subtilis | M. luteus | R. rubrum | S. epidermis |
|---|---|---|---|---|
| 1 | + | − | − | − |
| 2 | + | − | − | − |
| 3 | − | − | − | − |
| 4 | − | − | − | − |

TABLE 4

Presence of colonies after 4 days (+ or −)

| Plate Number | B. subtilis | M. luteus | R. rubrum | S. epidermis |
|---|---|---|---|---|
| 1 | + | − | − | − |
| 2 | + | − | − | − |
| 3 | − | − | − | − |
| 4 | − | − | − | − |

All controls produced the expected results, with positive control plates not treated with the sequentially-applied aqueous compositions containing the peracid reactant compounds showing growth for each organism characteristic of its growth within an open environment. Over the 16 control plates, there was an average of 4 colonies in the fourth quadrant of the plate, indicating that there were approximately 4,000,000 colonies in the initial inoculation.

Colonies were observed on two *B. subtilis* test plates after 1 day. However, these test plates were the ones that were inadvertently exposed to the ambient environment after the method was completed, but before the lids were sealed. These colonies possessed a different morphology than those on the *B. subtilis* control plates. Consequently, it is believed that these colonies represent a false positive, based on bacteria that were introduced onto the plates when the lids were inadvertently opened. Because colonies were found on plates that had previously been exposed to a peracid, these results also suggest that the test plates themselves were capable of supporting bacterial growth, and that the lack of observable colonies on the rest of the test plates is a direct consequence of the disinfection method employed in the experiment. Therefore, the lack of colonies on the rest of the test plates, coupled with the approximately 4,000,000 colonies observed on the control plates, indicates that the method was effective to at least a log-6 kill rate, representing a kill of at least 99.9999% of the bacteria originally present on the plate.

Example 4: Closed-System Control Experiments of Aqueous Compositions Containing Peracid Reactant Compounds A study was conducted in accordance with embodiments of the present disclosure to evaluate the individual contributions and potential synergistic effects of the peracid reactant compounds on the percent kill of *Bacillus subtilis* bacteria, using an electrostatic spray device. The electrostatic spray device used was a Hurricane ES™ Portable Electrostatic Aerosol Applicator, modified to selectively impart either a positive, negative, or neutral charge when dispersing an aqueous composition containing a peracid reactant compound. In experiments where multiple aqueous compositions containing peracid reactant compounds were dispersed, the compositions were dispersed sequentially, and all aqueous compositions were dispersed with either a positive, negative, or neutral charge, as indicated below in Table 5. The concentrations of each peracid reactant compound in the experiment indicated were identical to the concentrations reported in Example 2. In all experiments, the percent by weight of distilled water was adjusted appropriately in response to the addition or deletion of a peracid reactant compound. The testing area was sprayed with a volume of aqueous composition calculated to cover all surfaces with a 2-micron thickness, in order to limit the microbial kill enough to determine the effects of each peracid reactant compound. Processing and handling of the agar plates containing the *B. subtilis* bacteria was conducted according to the procedure used in Example 3.

TABLE 5

| Exp # | Treatments (charge) | | Percent Kill |
|---|---|---|---|
| 0 | Control w/ no treatment | | 0 |
| 1 | Hydrogen Peroxide (−) | Acetic Acid (+) | 87 |
| 2 | Hydrogen Peroxide (−) | Acetic Acid (+) | 90 |
| 3 | Hydrogen Peroxide (+) Ethanol | Acetic Acid (−) Ethanol | 94 |
| 4 | Hydrogen Peroxide (−) Ethanol | Acetic Acid (+) Ethanol | 96 |
| 5 | Acetic Acid (+) Ethanol | Hydrogen Peroxide (−) Ethanol | 95 |
| 6 | Acetic Acid (−) Ethanol | Hydrogen Peroxide (+) Ethanol | 92 |
| 7 | Hydrogen Peroxide only (No charge) | | 72 |
| 8 | Acetic Acid only (No charge) | | 6 |
| 9 | Ethanol only (No charge) | | 0 |

Comparison of the percent kill across all experiments illustrates several properties about the system, especially the synergistic effects that the peracid reactant compounds have when they are combined. Particularly, an approximate 10 percent increase in the percent kill of the bacteria is observed in the experiments where hydrogen peroxide and acetic acid are both dispersed (experiments 1 and 2) than where each component is applied on its own (experiments 7 and 8). This increase can be directly attributed to the formation of a peracid on the agar plates upon the sequential addition of both peracid reactant compounds. Furthermore, the addition of ethanol, which on its own had no effect on bacterial growth (experiment 9), caused the percent kill to go even higher when added to aqueous compositions containing hydrogen peroxide or acetic acid (experiments 3 through 6), independent of the order of addition or the charges imparted on a particular aqueous composition. Finally, while the experiments in which ethanol was added to hydrogen peroxide (experiments 3 through 6) all exhibited a percent kill above 90 percent, there appeared to be a slight preference for experiments in which acetic acid was applied with a positive charge and hydrogen peroxide was applied with a negative charge (experiments 4 and 5).

Example 5: Medium-Sized Area Electrospray Distribution Study

A study was conducted in accordance with embodiments of the present disclosure to evaluate the distribution of an aqueous composition containing 1% by weight acetic acid onto multiple target surfaces using an electrostatic spray device. The electrostatic spray device used was a Hurricane ES™ Portable Electrostatic Aerosol Applicator, modified to selectively impart either a positive, negative, or neutral charge. The laboratory space in which the testing surfaces were located was closed off to the surrounding environment and had a volume of about 30 cubic meters, approximately the size of a small hospital room. The electrospray device was placed on a platform approximately 2-feet high and approximately 5 feet from one of the corners of the laboratory space, and was pointed to face the opposite corner, enabling testing of distribution behind the electrospray device along the y-axis (defined below). Several pH testing strips were fixed throughout the laboratory space, particularly walls, floor, ceiling, and equipment, including exposed and non-exposed surfaces. The pH strips were evaluated both prior to and after electrospraying the acetic acid composition for a change in color in response to being exposed to the acetic acid composition. Each application of the acetic acid composition was sprayed with a negative charge.

For each application, the acetic acid composition was sprayed for approximately 45 seconds using a flow rate of 6 oz/min, which correlates with a droplet size of 10-20 microns, according to the instructions provided by the manufacturer of the Hurricane ES™ applicator. After spraying finished, researchers entered the room to evaluate the pH strips. Over three trials, every pH strip exhibited a color change during each trial, indicating that the acetic acid composition contacted each strip, even pH strips that were placed behind the electrospray device.

Figure 7:
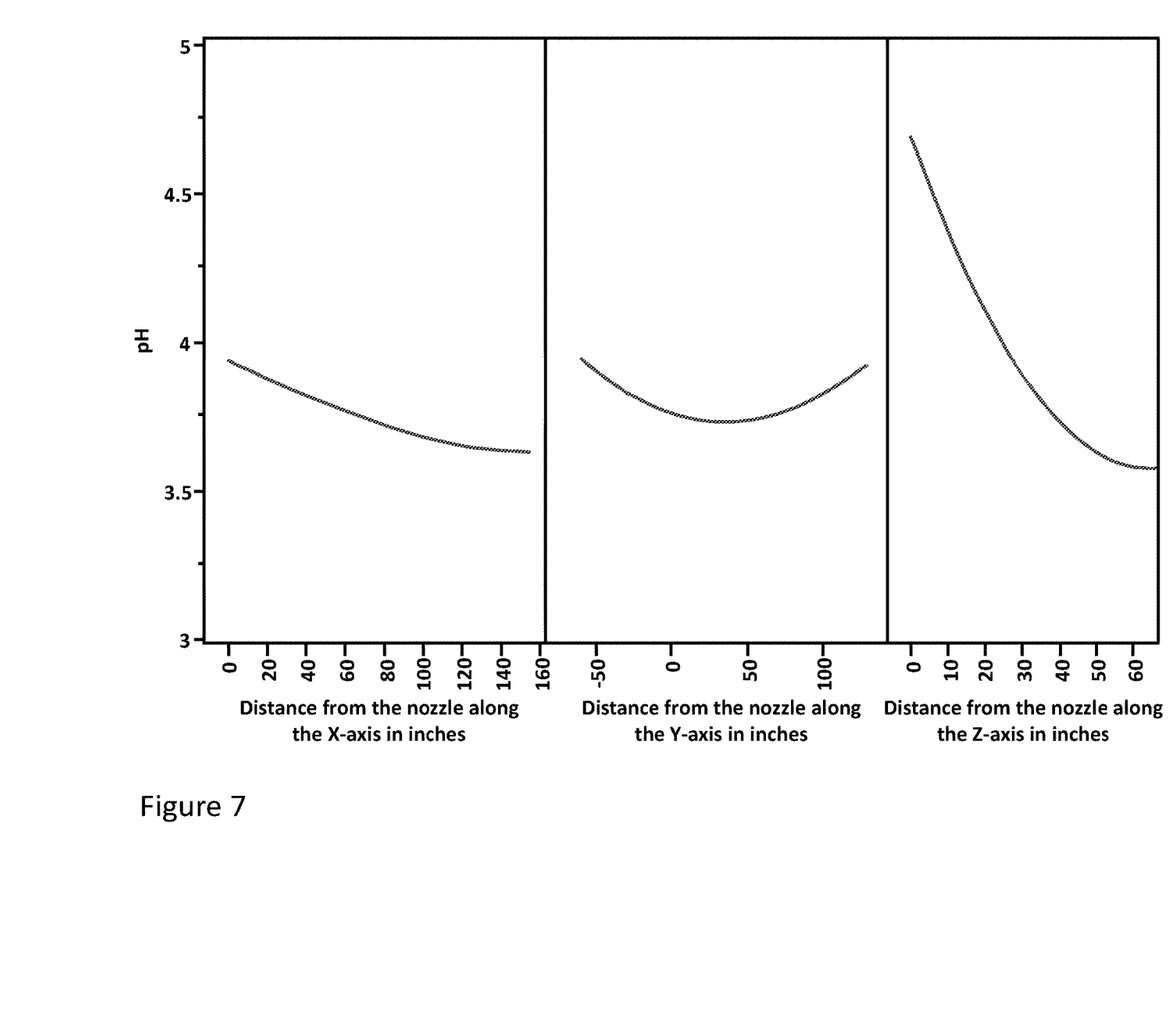
FIG. 7 shows the effect of distance on the dispersal of an aqueous composition along the x-, y-, and z-axis.

The pH at each pH strip location was quantified, and the pH distribution as a function of changes in x, y, and z direction from the nozzle on the electrospray device are shown in FIG. 7. Each of the lines represent a line of best fit of data collected from each of the pH strips within the area. A lower pH value indicates that more acetic acid contacted the pH strip at that location than at a location with a higher pH value. All distances were calculated in inches. The x-axis was defined as the horizontal axis perpendicular to the outward direction of the electrospray device. The y-axis was defined as the horizontal axis parallel to the outward direction of the electrospray device. The nozzle of the electrospray device was oriented to spray at a 45° angle relative to both the x- and y-axes. The z-axis is the vertical height extending directly upward or downward from the nozzle of the sprayer. Over both the x- and z-axes, contact by the acetic acid spray generally increased as the distance from the sprayer increased, as evidenced by the decreased pH measured at those locations. However, the effect was hyperbolic and flattened out after a time. Along the y-axis however, coverage generally decreased at a further distance away from the sprayer, although approximately the same decrease was observed both in front of (positive distance values) and behind (negative distance values) the electrospray. Nonetheless, in all cases, the difference between the pH at the greatest coverage and least coverage at the measured locations was narrow, although the effect was more pronounced along the z-axis.

Prophetic Examples

Example 6: Closed System Log-Kill of Methicillin-Resistant *Staphylococcus aureus* by Sequential Addition of the Aqueous Compositions of Example 2

A study is conducted in accordance with embodiments of the present disclosure to determine the antimicrobial activity against methicillin-resistant *Staphylococcus aureus* (MRSA) by sequentially applying the two aqueous compositions of Example 2 to form peracids in situ directly on surfaces to be disinfected within a closed system. The same protocol is used as performed in Example 3, except test plates contain MRSA instead of the strains tested in Example 3. It is expected that the same results are seen on all control and test plates as in Example 3.

Example 7: Medium-Sized Area Grounded-Surface Electrostatic Distribution Study

A study is conducted in accordance with embodiments of the present disclosure to evaluate the distribution of an aqueous composition containing 1% by weight acetic acid onto electrically-grounded target surfaces using an electrostatic spray device. Electrically-grounded metal objects, including metal trays, instruments, and hand rails are placed in the laboratory space, and pH strips are placed on both electrically-grounded and ungrounded surfaces. The composition and spraying procedure of Example 5 is used. It is expected that pH values observed on pH strips placed on grounded surfaces are substantially lower than pH values observed on pH strips on ungrounded surfaces, illustrating that a greater proportion of the acetic acid composition contacted the grounded surfaces.

Example 8: Medium-Sized Area Electrospray Log-Kill Study Using the Aqueous Compositions of Example 2

A study is conducted to determine the antimicrobial activity of producing peracids directly on surfaces to be disinfected in situ within a medium-sized area, using the aqueous compositions of Example 2. The protocol of Example 3 is used with the following modifications.

The area in which the surfaces are located is a hospital patient room, with a volume of about 100 to about 150 cubic meters. Test plates for each species are then placed at randomized x-, y-, and z-oriented locations throughout the room. An electrospray device with a compartment for each aqueous composition and adjustability between a positive and negative polarity is placed in the center of the room. Droplets of the first aqueous composition are electrostatically sprayed with a negative polarity for 1 minute, using a flow rate corresponding to a droplet size of about 15 microns. After waiting about 10 minutes to allow the first aqueous composition to deposit and coalesce in a layer on the test plates, the second aqueous composition is electrostatically sprayed with a positive polarity for 1 minute. After 1 minute, lids are placed on each of the test plates and immediately sealed with tape. It is expected that the same results are seen on all control and test plates as in Example 3.

We claim:
1. A method of disinfecting a surface in need of disinfecting within an area, comprising the steps of:
   a) dispersing into the area a multiplicity of droplets of a first aqueous composition comprising a first peracid reactant compound that is either hydrogen peroxide or an organic acid;
   b) allowing a time sufficient for the first aqueous composition to distribute throughout the area, and to deposit and coalesce into a layer upon the surface;
   c) dispersing into the area a multiplicity of droplets of a second aqueous composition comprising a second peracid reactant compound that is the other of the first peracid reactant compound; and d) allowing a second time sufficient for the droplets of the second aqueous composition to deposit onto the coalesced layer of the first aqueous composition to form a reaction layer, thereby forming a peracid in situ on the reaction layer and disinfecting the surface.

2. The method of claim 1, wherein an amount of the dispersed first aqueous composition is sufficient to provide the coalesced layer of the first aqueous composition with a substantially uniform thickness of at least about 1 micron, and up to about 20 microns.

3. The method of claim 2, wherein an amount of the dispersed second aqueous composition is sufficient to provide a coalesced layer of the second aqueous composition with a substantially uniform thickness of at least about 1 micron, and up to about 20 microns.

4. The method of claim 3, wherein the amount of the dispersed first aqueous composition is sufficient to provide the coalesced layer of the first aqueous composition with a substantially uniform thickness of at least about 3 microns, and up to about 8 microns.

5. The method of claim 3, wherein a stoichiometric amount of hydrogen peroxide in the reaction layer is equal to or greater than a stoichiometric amount of the organic acid in the reaction layer.

6. The method of claim 1, wherein a stoichiometric amount of the dispersed hydrogen peroxide is equal to or greater than a stoichiometric amount of the organic acid.

7. The method of claim 6, wherein the first aqueous composition comprises about 3% to about 7% by weight hydrogen peroxide.

8. The method of claim 7, wherein the second aqueous composition comprises about 5% to about 10% by weight acetic acid.

9. The method of claim 1, wherein the first aqueous composition comprises about 0.1% to about 25% by weight hydrogen peroxide.

10. The method of claim 9, wherein the second aqueous composition comprises about 0.5% to about 50% by weight acetic acid.

11. The method of claim 10, wherein at least one of the first aqueous composition or the second aqueous composition further comprises about 0.05% to about 25% by weight of a lower-chain alcohol, selected from the group consisting of ethanol, isopropanol, and t-butanol.

12. The method of claim 11, wherein the lower-chain alcohol comprises isopropanol.

13. The method of claim 1, wherein the multiplicity of droplets of the first aqueous composition are electrostatically-charged droplets.

14. The method of claim 13, wherein the multiplicity of electrostatically-charged droplets of the first aqueous composition are formed by spraying electrostatically the first aqueous composition.

15. The method of claim 14, wherein the multiplicity of electrostatically-charged droplets of the first aqueous composition are negatively charged.

16. The method of claim 14, wherein the multiplicity of electrostatically-charged droplets of the first aqueous composition are positively charged.

17. The method of claim 14, wherein the multiplicity of droplets of the second aqueous composition are electrostatically charged.

18. The method of claim 17, wherein the multiplicity of electrostatically-charged droplets of the second aqueous composition have an opposite polarity of the multiplicity of electrostatically-charged droplets of the first aqueous composition.

19. The method of claim 18, wherein the electrostatically-charged droplets of the first aqueous composition are negatively charged.

20. The method of claim 18, wherein the electrostatically-charged droplets of the first aqueous composition are positively charged.

21. The method of claim 14, wherein the surface in need of disinfecting is electrically grounded.

22. The method of claim 14, wherein an amount of the dispersed first aqueous composition is sufficient to provide the coalesced layer of the first aqueous composition with a substantially uniform thickness of at least about 3 microns.

23. The method of claim 22, wherein an amount of the dispersed second aqueous composition is sufficient to provide a coalesced layer of the second aqueous composition with a substantially uniform thickness of at least about 3 microns.

24. The method of claim 23, wherein a stoichiometric amount of the hydrogen peroxide is equal to or greater than a stoichiometric amount of the organic acid.

25. The method of claim 14, wherein the first aqueous composition comprises about 0.1% to about 25% by weight hydrogen peroxide.

26. The method of claim 25, wherein the second aqueous composition comprises about 0.5% to about 50% by weight acetic acid.

27. The method of claim 26, wherein at least one of the first aqueous composition or the second aqueous composition further comprises about 0.05% to about 25% by weight of a lower-chain alcohol, selected from the group consisting of ethanol, isopropanol, and t-butanol.

28. The method of claim 27, wherein the lower-chain alcohol comprises isopropanol.

29. The method of claim 1, wherein the pH of the aqueous composition comprising the organic acid is less than or equal to about 7.

30. The method of claim 29, wherein the organic acid is selected from the group of carboxylic acids consisting of formic acid, acetic acid, citric acid, oxalic acid, propanoic acid, lactic acid, butanoic acid, pentanoic acid, octanoic acid, including mixtures thereof.

* * * * *